United States Patent
Saito et al.

(10) Patent No.: US 7,662,957 B2
(45) Date of Patent: Feb. 16, 2010

(54) METHOD FOR PRODUCING 3,4-DIHYDRO-1,2,3-OXATHIAZIN-4-ONE-2,2-DIOXIDE COMPOUND OR SALT THEREOF

(75) Inventors: Akira Saito, Myoko (JP); Yuki Ishiguro, Myoko (JP); Yasushi Yamamoto, Myoko (JP)

(73) Assignee: Daicel Chemical Industries, Ltd., Osaka-shi (JP)

( * ) Notice: Subject to any disclaimer, the term of this patent is extended or adjusted under 35 U.S.C. 154(b) by 0 days.

(21) Appl. No.: 12/373,922

(22) PCT Filed: Aug. 2, 2007

(86) PCT No.: PCT/JP2007/065138

§ 371 (c)(1),
(2), (4) Date: Jan. 15, 2009

(87) PCT Pub. No.: WO2008/016100

PCT Pub. Date: Feb. 7, 2008

(65) Prior Publication Data

US 2009/0318685 A1    Dec. 24, 2009

(30) Foreign Application Priority Data

Aug. 3, 2006    (JP) ............... 2006-212263

(51) Int. Cl.
*C07D 291/06* (2006.01)
(52) U.S. Cl. ............................. 544/2; 562/40
(58) Field of Classification Search ...... 544/2; 562/40
See application file for complete search history.

(56) References Cited

U.S. PATENT DOCUMENTS

| | | | |
|---|---|---|---|
| 4,804,755 A | 2/1989 | Reuschling et al. | |
| 4,806,639 A | 2/1989 | Reuschling et al. | |
| 4,876,341 A | 10/1989 | Schutz et al. | |
| 2005/0182255 A1 | 8/2005 | Kobayashi et al. | |

FOREIGN PATENT DOCUMENTS

| JP | 62-56480 A | 3/1987 |
|---|---|---|
| JP | 62-56481 A | 3/1987 |
| JP | 62-129277 A | 6/1987 |
| JP | 2003-2879 A | 1/2003 |
| JP | 2005-263779 A | 9/2005 |

*Primary Examiner*—Kahsay T Habte
(74) *Attorney, Agent, or Firm*—Birch, Stewart, Kolasch & Birch, LLP

(57) ABSTRACT

A high quality 3,4-dihydro-1,2,3-oxathiazin-4-one-2,2-dioxide compound or a salt thereof is obtained easily and efficiently.

When the compound represented by the following formula (2)
[Formula 2]

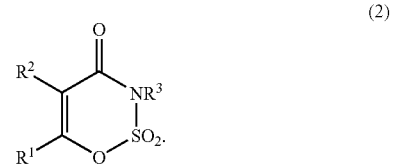

(wherein, $R^1$, $R^2$, and $R^3$ are hydrogen atom or an organic group inert to the reaction, and X is hydrogen atom) or a salt thereof is produced by cyclization of a mixture of β-ketoamide-N-sulfonic acid represented by the following formula (1)
[Formula 1]

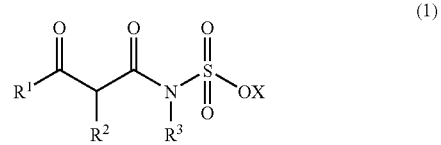

or a salt thereof and an inert solvent and a mixture of acid anhydride and an inert solvent, and by subsequent hydrolysis of the product, a step of (A) hydrolyzing the reaction product obtained by the cyclization by mixing with an aqueous solution of sulfuric acid so as a concentration of sulfuric acid in an aqueous phase after the hydrolysis would become 30% by weight or more, and then separating an organic phase and an aqueous phase, or a step of (B) washing the organic phase liquid after the hydrolysis with an aqueous solution of sulfuric acid with a concentration of 30% by weight or more is at least carried out.

4 Claims, No Drawings

METHOD FOR PRODUCING 3,4-DIHYDRO-1,2,3-OXATHIAZIN-4-ONE-2,2-DIOXIDE COMPOUND OR SALT THEREOF

TECHNICAL FIELD

The present invention relates to a method for producing 3,4-dihydro-1,2,3-oxathiazin-4-one-2,2-dioxide compounds or salts thereof which are useful as sweeteners or raw materials therefore in food industry or intermediate materials for fine chemicals or the like.

BACKGROUND ART

As for a method for producing a 3,4-dihydro-1,2,3-oxathiazin-4-one-2,2-dioxide compound and a salt thereof, Patent Documents 1 to 3 disclose the method in which acetoacetamide-N-sulfonic acid or a salt thereof is reacted with $SO_3$ in an inert organic solvent to cyclize and ring-close, and then the product is hydrolyzed to produce 6-methyl-3,4-dihydro-1,2,3-oxathiazin-4-one-2,2-dioxide or a salt thereof. In this method, the hydrolysis is carried out by mixing the reaction product of the ring closure process and water, and the 3,4-dihydro-1,2,3-oxathiazin-4-one-2,2-dioxide compound is obtained from an organic solvent obtained by liquid-liquid separation after the hydrolysis. Furthermore, Patent Document 1 discloses that the organic solvent obtained by the liquid-liquid separation after the hydrolysis may be purified by extraction using water or a dilute aqueous sulfuric acid.

However, when water is used for the hydrolysis of the cyclized product, the organic solvent obtained by the liquid-liquid separation after the hydrolysis is colored remarkably, so that purification loads for the target compound after the hydrolysis are increased. Furthermore, even if the organic solvent is extracted using water or the dilute aqueous sulfuric acid, hue of the organic solvent is not so improved.

Patent Document 1: Japanese Unexamined Patent Publication No. 62-56481.
Patent Document 2: Japanese Unexamined Patent Publication No. 62-129277.
Patent Document 3: Japanese Unexamined Patent Publication No. 2005-263779.

DISCLOSURE OF THE INVENTION

Technical Problems to be Solved

An object of the present invention is to provide a method for producing a high quality 3,4-dihydro-1,2,3-oxathiazin-4-one-2,2-dioxide compound or a salt thereof easily and efficiently.

Means to Solve the Problems

After intensive investigations to achieve the above object, the present inventors have found that a solution of organic solvent containing the target compound with less coloring and fine hue may be obtained easily and efficiently when the reaction product obtained by the cyclization is hydrolyzed by mixing with an aqueous solution of sulfuric acid so that a concentration of sulfuric acid in the aqueous phase liquid after the hydrolysis would become a specified concentration or higher, and then an organic phase liquid and an aqueous phase liquid are separated or the organic phase liquid after the hydrolysis is washed with an aqueous solution of sulfuric acid with a specified concentration. Consequently the present inventors have completed the present invention.

Specifically, the present invention provides a method for producing a 3,4-dihydro-1,2,3-oxathiazin-4-one-2,2-dioxide compound or a salt thereof. The 3,4-dihydro-1,2,3-oxathiazin-4-one-2,2-dioxide compound is represented by the following formula (2).

[Formula 2]

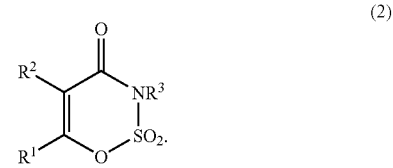

In the formula (2), $R^1$ and $R^2$ are the same as or different from each other and are each hydrogen atom or an organic group inert to a reaction, $R^3$ is hydrogen atom or an organic group inert to the reaction. The 3,4-dihydro-1,2,3-oxathiazin-4-one-2,2-dioxide compound or a salt thereof is produced by mixing a first solution of β-ketoamide-N-sulfonic acid or a salt thereof dissolved or dispersed in an inert solvent and a second solution of acid anhydride dissolved or dispersed in an inert solvent to be carried out cyclization, and subjecting the cyclized product to hydrolysis to obtain a mixed solution containing a liquid in organic phase and a liquid in aqueous phase. The β-ketoamide-N-sulfonic acid is represented by the following formula (1).

[Formula 1]

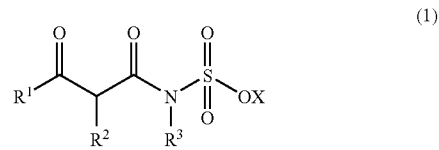

In the formula (1), $R^1$, $R^2$ and $R^3$ are as defined above, and X is hydrogen atom. The method of the present invention comprises at least one step selected from a group consisting of: Step(A) of hydrolyzing the cyclized product by mixing with an aqueous solution of sulfuric acid so that a concentration of the sulfuric acid in the liquid in aqueous phase after the hydrolysis would become 30% by weight or more, and separating the mixed solution to the liquid in organic phase and the liquid in aqueous phase; and Step(B) of washing the liquid in organic phase after the hydrolysis with an aqueous solution of sulfuric acid with a concentration of 30% by weight or more.

In the method, preferably, a concentration of the aqueous solution of sulfuric acid used in Step (A) is 15 to 50% by weight. Further, preferably, a concentration of the aqueous solution of sulfuric acid used in Step (B) is 45 to 80% by weight.

Further, preferably, the aqueous solution of sulfuric acid used in Step (A) is a solution obtained in Step (B) after washing.

EFFECT OF THE INVENTION

According to the present invention, an aqueous solution of sulfuric acid with a specified concentration is used for the hydrolysis of the cyclized product and/or for the washing of the organic solvent after the hydrolysis, so that hue of the organic solvent solution containing the target compound is improved and purification loads after the washing are reduced significantly.

BEST MODE FOR CARRYING OUT THE INVENTION

In the present invention, a solution containing β-ketoamide-N-sulfonic acid represented by Formula (1) or a salt thereof dissolved or dispersed in an inert solvent and a solution containing acid anhydride dissolved or dispersed in an inert solvent are subjected to cyclization and then further subjected to hydrolysis to produce the 3,4-dihydro-1,2,3-oxathiazin-4-one-2,2-dioxide compound represented by Formula (2) or a salt thereof.

In Formula (1), the organic group inert to the reaction in $R^1$, $R^2$ and $R^3$ to be used is not limited as long as the organic groups are inert to the reaction. Examples of the organic group inert to the reaction contain alkyl groups, alkenyl groups, alkynyl groups, cycloalkyl groups, acyl groups, aralkyl groups, aryl groups, and the like. The alkyl groups include straight or branched chain $C_{1-10}$ alkyl groups (for example, $C_{1-6}$ alkyl groups such as methyl group, ethyl group, propyl group, butyl group, isobutyl group, tert-butyl group). The alkenyl groups include straight or branched chain $C_{2-10}$ alkenyl groups (for example, $C_{2-5}$ alkenyl groups such as vinyl group, allyl group, isopropenyl group, 1-butenyl group, 2-butenyl group). The alkynyl groups include straight or branched chain $C_{2-10}$ alkynyl groups (for example, $C_{2-5}$ alkynyl groups such as ethynyl group, propynyl group, 1-butynyl group, 2-butynyl group). The cycloalkyl groups include, for example, $C_{3-10}$ cycloalkyl groups such as cyclopropyl group, cyclobutyl group, cyclopentyl group, and cyclohexyl group (preferably, $C_{4-8}$ cycloalkyl groups). The acyl groups include straight or branched chain $C_{2-10}$ aliphatic acyl groups (for example, acetyl group, propionyl group, butyryl group, isobutyryl group, and valeryl group), or $C_{7-11}$ aromatic acyl groups (for example, benzoyl group, toluoyl group, and naphthoyl group), and the like. The aralkyl groups include $C_{6-10}$ aryl-$C_{1-4}$ alkyl groups (for example, benzyl group) and the like, and the aryl groups include $C_{6-10}$ aryl groups such as phenyl group.

The salt of β-ketoamide-N-sulfonic acid compound represented by Formula (1) includes salts (sulfonates) in which the sulfonic group is neutralized with a base, and salts in which, when $R^3$ is hydrogen atom, the —NH— group in the formula is neutralized with a base. Examples of these salts (salts of sulfonic acid, and salts of —NH—) are metal salts, ammonium salts, salts of organic bases, and the like. Examples of the metal salts are salts of alkali metals (Group 1A metals of the Periodic Table) such as Li, Na, and K; salts of alkaline earth metals (Group 2A metals of the Periodic Table) such as Mg, Ca, Sr, and Ba; salts of metals of Group 3B of the Periodic Table such as Al, and Ga; and salts of transition metals (for example, Group 3A metals, Group 4A metals, Group 5A metals, Group 6A metals, Group 7A metals such as Mn, Group 8 metals such as Fe, Group 1B metals such as Cu, Ag, and Au, Group 2B metals such as Zn, Group 4B metals, Group 5B metals of the Periodic Table) and the like. Preferred metal salts include salts of mono-, di- or tri-valent metals, for example, salts of alkali metals (Na, K, and the like), salts of alkaline earth metals (Mg, Ca, and the like), Al salts, and salts of transition metals (Mn, Fe, and the like). In consideration of economical efficiency, safety, and the like, salts of alkali metals such as Na and K are especially preferred.

Examples of the organic bases are aliphatic amines [primary amines (for example, $C_{1-10}$ monoalkylamines such as methylamine and ethylamine), secondary amines (for example, di-$C_{1-10}$ alkylamines such as dimethylamine and ethylmethylamine), and tertiary amines (for example, tri-$C_{1-10}$ alkylamines such as trimethylamine and triethylamine)], alicyclic amines (for example, mono-, di-, or tri-$C_{3-12}$ cycloalkylamines such as cyclohexylamine), aromatic amines (for example, mono-$C_{6-10}$ arylamines such as aniline and dimethylaniline, di-$C_{6-10}$ arylamines such as diphenylamine, tri-$C_{6-10}$ arylamines such as triphenylamine, and aralkylamines such as benzylamine), cyclic amines (for example, piperidine, N-methylpiperidine, and morpholine), and nitrogen-containing aromatic heterocyclic compounds (for example, pyridine, quinoline, or derivatives thereof). Preferred organic bases include aliphatic amines. Furthermore, not only aliphatic tertiary amines but also any tertiary amine is preferred.

In Formula (1), $R^1$ to $R^3$ may be composed of any suitable combination, and for example, a combination in which $R^1$ and $R^2$ are each hydrogen atom or a $C_{1-4}$ alkyl group, and $R^3$ is hydrogen atom or a $C_{1-4}$ alkyl group is preferred. Among them, as for the compound represented by Formula (1), acylacetoamide-N-sulfonic acid in which $R^1$ is a $C_{1-4}$ alkyl group and $R^2$ and $R^3$ are hydrogen atoms is preferred, and specifically, acetoacetamide-N-sulfonic acid in which $R^1$ is methyl group is preferred. As for the salt (sulfonate) of the compound represented by Formula (1), specifically, a salt with a tertiary amine is preferred.

In the invention, the acid anhydride works as a cyclizing agent (cyclization-dehydration agent and the like) for β-ketoamide-N-sulfonic acid represented by Formula (1) or a salt thereof (hereinafter, sometimes simply referred to as "substrate"). Examples of the acid anhydride are acid anhydrides formed from inorganic acids such as sulfuric acid, halogenated sulfuric acids (fluorosulfuric acid, chlorosulfuric acid, and the like), pyrophosphoric acids (pyrophosphoric acid; and halogenated pyrophosphoric acids such as fluoropyrophosphoric acid), nitric acid, and boric acids (orthoboric acid, metaboric acid, and the like); and formed from organic acids such as sulfonic acids, organic phosphoric acids ($C_{1-4}$ alkylphosphoric acids such as methylphosphoric acid; phosphoric acid mono-$C_{1-4}$ alkyl esters such as phosphoric acid monomethyl ester and phosphoric acid monoethyl ester); and the like. The acid anhydride may be any of an acid anhydride formed from elimination of water from one molecule of an acid, an acid anhydride formed from elimination of water from two or more molecules of an acid, and an acid anhydride formed from elimination of water from two or more molecules of different acids (mixed acid anhydride), and the like. The acid anhydrides may be used alone or as a mixture of two or more acid anhydrides. Preferred acid anhydride is the acid anhydride formed from an acid containing sulfuric acid, and sulfuric anhydride ($SO_3$) is especially preferred.

An amount of the acid anhydride used is generally at least 1 mol or more (for example, from about 1 to about 20 mol), preferably from about 1 to about 10 mol, and specifically preferably from about 4 to about 8 mol per 1 mol of the substrate.

The cyclization (cyclization-dehydration and the like) of β-ketoamide-N-sulfonic acid represented by Formula (1) or a salt thereof is carried out in the presence of a solvent. As the reaction solvent, various inorganic and organic solvents inert to the reaction (specifically, not reacting with acid anhydride) may be used, but generally an organic solvent inert to the reaction is used. Furthermore, as the reaction solvent, generally, a solvent containing substantially no water is used.

In the invention, an inert solvent in which β-ketoamide-N-sulfonic acid represented by Formula (1) or a salt thereof is dissolved or dispersed and an inert solvent in which the acid anhydride is dissolved or dispersed may be the same as or different from each other. Examples of the inert solvent are aliphatic hydrocarbons (for example, pentane, hexane, and octane), alicyclic hydrocarbons (for example, cyclohexane), aromatic hydrocarbons (for example, benzene, toluene, xylene, and ethylbenzene), halogenated hydrocarbons (for example, haloalkanes such as dichloromethane, dichloroethane, chloroform, trichloroethylene, tetrachloroethylene, and trichlorofluoroethylene), esters (for example, carboxylic esters such as methyl acetate, ethyl acetate, butyl acetate, and methyl propionate), ketones (for example, aliphatic ketones such as acetone, methyl ethyl ketone, and methyl isobutyl ketone; and cyclic ketones such as cyclohexanone), ethers (for example, chain ethers such as diethyl ether, diisopropyl ether, 1, 2-dimethoxyethane, cellosolve, carbitol, diglyme, and diethylene glycol dimethyl ether; aromatic ethers such as anisole, 1,2-dimethoxybenzene, and diphenyl ether; and cyclic ethers such as tetrahydrofuran, dioxolane, and dioxane), sulfoxides (for example, dimethyl sulfoxide, sulfolane, 2-methylsulfolane, and 3-methylsulfolane) and the like. These solvents may be used alone or as a mixture of two or more solvents. Preferred solvents are halogenated hydrocarbons, and specifically preferably dichloromethane is used.

It is preferred that the cyclization is carried out continuously using a continuous flow reactor. A tubular reactor or a motionless mixer is preferably used as the continuous flow reactor. In order to get a better result of the cyclization, it is preferred that the substrate and the acid anhydride to be used in the reaction are dissolved or dispersed in the above-mentioned solvents to obtain solutions, respectively.

The each obtained solution is cooled to, for example, 10° C. or below (from about −100° C. to about 10° C.), preferably from −80° C. to 10° C. and specifically preferably from −30° C. to 10° C. before the reaction. The concentration of the substrate in the solution containing the substrate to be fed into the reactor may be appropriately selected in a range not deteriorating operability and the like, and is generally from about 0.1 to about 50% by weight, preferably from about 0.5 to about 30% by weight, and more preferably from about 1 to about 20% by weight (specifically from about 5 to about 15% by weight). The concentration of the acid anhydride in the solution containing the acid anhydride to be fed into the reactor may be appropriately selected in a range not deteriorating operability and the like, and is generally from about 0.1 to about 50% by weight, preferably from about 0.5 to about 30% by weight, and more preferably from about 5 to about 20% by weight.

The total used amount of the reaction solvent may be appropriately selected in consideration of reactivity and operability, and generally may be selected in a wide range from about 1 to about 1000 parts by weight per 1 part by weight of the substrate, and is preferably from about 5 to about 500 parts by weight, more preferably from about 10 to about 100 parts by weight, and specifically preferably from about 15 to about 50 parts by weight.

The cyclization is preferably carried out by continuously feeding a mixture of the solutions of β-ketoamide-N-sulfonic acid represented by Formula (1) or a salt thereof with an inert solvent and acid anhydride with an inert solvent into a tubular flow reactor or a motionless mixer. The tubular flow reactor or motionless mixer may be equipped with a cooler such as a cooling jacket and a cooling tank (refrigerant tank) so as to cool the reactor from the outside. The reaction temperature of the cyclization may be set appropriately in consideration of reaction rate and the like.

For the tubular reactor, for example, a common stainless steel tube and a lined tube lined with glass, Teflon (registered trademark) or the like may be used, but the material for the tubular reactor is not limited to these materials. Furthermore, the inner diameter of the tube to be used is not specifically limited, but it is preferable that, in consideration of removal of reaction heat during the cyclization, the inner diameter is preferably several tens of mm or less (for example, from about 0.2 to about 30 mm) and specifically preferably 10 mm or less (for example, from about 0.2 to about 10 mm).

Furthermore, the length of the tube is set so as to satisfy the need for a residence time required for the reaction. The residence time is from about 0.001 to about 60 seconds, preferably from 0.01 to 40 seconds, and more preferably from 0.1 to 10 seconds (specifically from 1 to 10 seconds). The residence time (sec) is a value determined by the equation: [capacity of the reactor (ml)]/[total fed amount of raw material mixture (ml/sec)].

The tubular reactor may be equipped with an apparatus for accelerating a mixing of β-ketoamide-N-sulfonic acid represented by Formula (1) or a salt thereof with the acid anhydride, at an inlet part of the tubular reactor. Examples of the apparatus are stirring mixers, ultrasonic mixers, motionless mixers such as a static mixer, and piping joints (hereinafter, sometimes simply referred to as "premixer"). When the premixer is equipped at the inlet part of the tubular reactor, the residence time in the premixer is, for example, from about 0.0005 to about 30 seconds, preferably from about 0.01 to about 20 seconds, and more preferably from about 0.1 to about 10 seconds (specifically from about 1 to about 10 seconds), and the subsequent residence time in the tubular reactor is, for example, from about 0.001 to about 60 seconds, preferably from about 0.01 to about 40 seconds, and more preferably from about 0.1 to about 30 seconds (specifically from about 1 to about 30 seconds).

Furthermore, in the invention, a motionless mixer such as a static mixer may also be used as the reactor. When the motionless mixer is used as the reactor, a motionless mixer with a larger inner diameter than that of the tubular reactor may be used since the motionless mixer can remove the reaction heat sufficiently. For example, the inner diameter of the motionless mixer is from about 0.2 to about 30 mm, and preferably from about 0.5 to about 20 mm. A type of the motionless mixer is not specifically limited, but as a typical motionless mixer, a Sulzer static mixer, a Kenics static mixer and the like may be used. When the motionless mixer is used as the reactor, the residence time is, for example, from about 0.001 to about 60 seconds, preferably from about 0.01 to about 40 seconds, and more preferably from about 0.03 to 10 seconds. In this case, such premixer described above may also be equipped at the inlet part of the motionless mixer. In this case, the residence time in the premixer is, for example, from about 0.0005 to about 30 seconds, preferably from about 0.01 to about 20 seconds, and more preferably from about 0.1 to about 10 seconds (specifically from about 1 to about 10 seconds), and the subsequent residence time in the motionless mixer is, for example, from about 0.001 to about 60 seconds, preferably from about 0.01 to about 40 seconds, and more preferably from about 0.03 to about 10 seconds.

The number of elements in the static mixer is not specifically limited, but is, for example, 5 or more (from about 5 to about 25), and preferably 10 or more.

By the above mentioned cyclization, generally, elimination of water or a base [for example, in the case that a salt of the compound represented by Formula (1) is used as the substrate] derives the 3,4-dihydro-1,2,3-oxathiazin-4-one-2,2-dioxide compound represented by Formula (2). In this case, according to the type or the amount of the acid anhydride used, an adduct or the like of the 3,4-dihydro-1,2,3-oxathiazin-4-one-2,2-dioxide compound represented by Formula (2) with the acid anhydride may be formed. In this case, after the cyclization, subsequent hydrolysis of the adduct may derive the 3,4-dihydro-1,2,3-oxathiazin-4-one-2,2-dioxide compound represented by Formula (2).

The hydrolysis is carried out by, for example, subjecting the reaction mixture obtained by the cyclization to mixing with water or a solution containing water (for example, an aqueous solution of sulfuric acid), if required, after a suitable treatment of the reaction mixture. The hydrolysis may be carried out by any system such as continuous system, batch system or semi-batch system. The continuous hydrolysis may be carried out with not only a stirring tank but also the continuous processor used for the cyclization. The temperature and the reaction temperature of water or the solution containing water to be used in the hydrolysis are, for example, from 0° C. to 50° C. and preferably from 10° C. to 40° C. Furthermore, the amount of water (or the amount of water contained in the solution containing water) is, for example, from about 1 mol to about 100 mol, preferably from about 1 mol to about 50 mol, and more preferably from about 2 mol to about 20 mol per 1 mol of the acid anhydride used in the cyclization. Water may be used in large excess. The reaction time of the hydrolysis (in the case of continuous system, residence time) is, for example, 1 hour or less (from about 0.1 minute to about 1 hour), and preferably from about 1 minute to about 10 minutes.

The 3,4-dihydro-1,2,3-oxathiazin-4-one-2,2-dioxide compound represented by Formula (2) obtained in this manner may be separated and purified by a separation means such as washing, liquid-liquid separation, concentration, solvent exchange, extraction, crystallization, recrystallization, and column chromatography. For example, the target compound may be isolated by the following procedures; the reaction mixture after the completion of the hydrolysis is separated into an organic phase liquid (inert solvent phase liquid) containing the target compound and an aqueous phase liquid, the organic phase liquid is washed with water or a solution containing water (for example, an aqueous solution of sulfuric acid), and then operations such as concentration, solvent exchange, crystallization are carried out. Furthermore, the target compound remaining in the aqueous phase liquid may be extracted and collected by adding a solvent incompatible (or immiscible) with water [the solvent used for the cyclization or esters of an organic monocarboxylic acid or an organic dicarboxylic acid (for example, the esters listed in the description of the reaction solvent) and the like] to the aqueous phase liquid.

An important feature of the producing method of the invention is that the steps after the cyclization include at least one step selected from the group consisting of (A) hydrolyzing the reaction product obtained by the cyclization by mixing with an aqueous solution of sulfuric acid so that the concentration of sulfuric acid in an aqueous phase liquid after the hydrolysis would be 30% by weight or more, and then separating the mixture in an organic phase liquid and an aqueous phase liquid, and (B) washing the organic phase liquid after the hydrolysis with an aqueous solution of sulfuric acid with a concentration of 30% by weight or more. In the liquid-liquid separation of the reaction mixture after the hydrolysis into the organic phase liquid (containing the target compound) and the aqueous phase liquid in Step (A), the clear liquid-liquid separation is achieved and transfer or distribution of impurities (for example, colored materials) to the organic phase liquid is inhibited, so that the organic phase liquid (the solution containing the target compound) with fine hue (less coloring) and less impurities may be obtained. According to Step (B), the impurities (for example, colored materials) contained in the organic phase liquid is transferred into the aqueous phase liquid including the aqueous solution of sulfuric acid, so that the hue or the impurity content of the organic phase liquid is improved significantly. Therefore, the carrying out of Step (A) and/or Step (B) simplifies the subsequent purification step and reduces the purification loads, so that the target compound with high quality can be obtained easily and efficiently. In more specific description, the coloring components caused by the cyclization and the hydrolysis have a feature in which the components are hard to be removed by the subsequent purification step such as crystallization operation and activated carbon treatment. Furthermore, generally, the compound represented by Formula (2) is derived to a salt thereof, and if the compound represented by Formula (2) contains the coloring components, the crystallization operation has to be carried out many times for decoloration even in the purification step of the salt thereof. Furthermore, during the crystallization operation for the purification of the salt, a large amount of the product is lost in a filtrate and the yield is reduced, so that the filtrate has to be reused in the producing step of the salt. However, the reuse of the filtrate is difficult because the coloring components make the hue of the crystallization filtrate of the salt remarkably deteriorate. According to the producing method of the invention, the coloring components can be removed efficiently, so that the number of the subsequent crystallization operations of the salt of the compound represented by Formula (2) can be reduced to, for example, once or twice, and the purification step can be simplified. Furthermore, the filtrate by the crystallization operation can be reused, so that the yield is improved.

The producing method of the invention include at least one step of Step (A) and Step (B). For example, in the case that Step (A) is carried out, the aqueous solution of sulfuric acid with a concentration of 30% by weight or more does not always have to be used for the washing of the organic phase liquid after the hydrolysis, for example, water and an aqueous solution of sulfuric acid with a concentration of less than 30% by weight may be used for the washing, and the washing step may be skipped. Furthermore, in the case that Step (B) is carried out, the hydrolysis of the reaction product obtained by the cyclization does not always have to be carried out by mixing with an aqueous solution of sulfuric acid so that the concentration of sulfuric acid in the aqueous phase liquid after the hydrolysis would become 30% by weight or more, and for example the hydrolysis may be carried out using water. However, in order to obtain the target compound with higher quality, more easily and more efficiently, it is preferred that both Step (A) and Step (B) are carried out.

In Step (A), it is preferred that the concentration of sulfuric acid in the aqueous phase liquid after the hydrolysis is 30% by weight or more (for example, from 30 to 80% by weight), preferably from 35 to 75% by weight, more preferably from 40 to 70% by weight, and specifically preferably from 45 to 70% by weight. If the concentration of sulfuric acid in the aqueous phase liquid after the hydrolysis is too low, the hue of the organic phase liquid obtained by the liquid-liquid separation is apt to become deteriorated and the liquid-liquid separation is also apt to become difficult. On the other hand, if the concentration of sulfuric acid in the aqueous phase liquid after the hydrolysis is too high, the organic phase liquid after the liquid-liquid separation sometimes becomes cloudy or the liquid-liquid separation sometimes becomes difficult. The concentration of the aqueous solution of sulfuric acid used for the hydrolysis is preferably from about 15 to about 50% by weight, more preferably about 20 to about 45% by weight, and specifically preferably about 20 to about 40% by weight. If the concentration of the aqueous solution of sulfuric acid used for the hydrolysis is too low, the hue of the obtained organic phase liquid is apt to become deteriorated, and the liquid-liquid separation is also apt to become difficult. On the other hand, if the concentration of the aqueous solution of sulfuric acid used for the hydrolysis is too high, the organic phase liquid sometimes becomes cloudy, the liquid-liquid separation sometimes becomes difficult, or a distribution factor of the target compound to the organic phase liquid is sometimes reduced. The amount of the aqueous solution of sulfuric acid used for the hydrolysis is any amount as long as the amount of water required for the hydrolysis would be contained and the concentration of sulfuric acid after the hydrolysis would become within the above-mentioned range. For example, the amount of the aqueous solution of sulfuric acid used for the hydrolysis varies according to the type or the used amount of the acid anhydride or the like, but is generally from about 80 to about 400 parts by weight, and preferably from about 100 to about 300 parts by weight per 100 parts by weight of the used amount of the acid anhydride.

In Step (B), the concentration of the aqueous solution of sulfuric acid used for the washing of the organic phase liquid after the hydrolysis is 30% by weight or more (for example, from 30 to 80% by weight), preferably from 45 to 80% by weight, more preferably from 50 to 80% by weight, and specifically preferably from 60 to 78% by weight. If the concentration of the aqueous solution of sulfuric acid used for the washing is too low, the improvement effect of the hue of the organic phase liquid is small and the liquid-liquid separation is also apt to become difficult. On the other hand, if the concentration of the aqueous solution of sulfuric acid used for the washing is too high, the organic phase liquid sometimes becomes cloudy or the liquid-liquid separation sometimes becomes difficult. The amount of the aqueous solution of sulfuric acid used for the washing is, for example, from about 1 to about 100 parts by weight, and preferably from about 2 to about 50 parts by weight per 100 parts by weight of the organic phase liquid fed to the washing. From the washed liquid in the organic phase, the target compound with high quality may be obtained by the above-mentioned operations such as concentration, solvent exchange, and crystallization.

The washing solution after the washing in Step (B) may be used without any treatment or with appropriate dilution or concentration, as the aqueous solution of sulfuric acid for the hydrolysis in Step (A). The usage of the washing solution as the aqueous solution of sulfuric acid for the hydrolysis may significantly reduce the waste amount to be handled or the waste amount to be disposed, and may collect the compound represented by Formula (2) contained in the washing solution.

A salt of the 3,4-dihydro-1,2,3-oxathiazin-4-one-2,2-dioxide compound represented by Formula (2) may be obtained by a common salt-forming reaction such as a reaction of the compound represented by Formula (2) (compound with $R^3$ being hydrogen atom) with a base. Examples of the salt of the 3,4-dihydro-1,2,3-oxathiazin-4-one-2,2-dioxide compound represented by Formula (2) are metal salts, ammonium salts, and salts of organic bases. The types and preferred examples of the metal salts and the organic bases are the same as in the case of the salts of β-ketoamide-N-sulfonic acid represented by Formula (1). Specially preferred salts are salts of alkali metals such as sodium, and potassium salts.

The alkali metal salts of the 3,4-dihydro-1,2,3-oxathiazin-4-one-2,2-dioxide compound represented by Formula (2) may be obtained by a reaction of the compound represented by Formula (2) (compound with $R^3$ being hydrogen atom) with a base containing alkali metal such as alkali metal hydroxides (sodium hydroxide, potassium hydroxide, and the like), alkali metal carbonates (sodium carbonate, potassium carbonate, and the like), alkali metal hydrogen carbonates (sodium hydrogen carbonate, potassium hydrogen carbonate, and the like).

The salt of the 3,4-dihydro-1,2,3-oxathiazin-4-one-2,2-dioxide compound represented by Formula (2) may be separated and purified by separation means such as concentration, extraction, crystallization, recrystallization, column chromatography, and the like.

Typical examples of the 3,4-dihydro-1,2,3-oxathiazin-4-one-2,2-dioxide compound represented by Formula (2) or a salt thereof are 6-$C_{1-4}$ alkyl-3,4-dihydro-1,2,3-oxathiazin-4-one-2,2-dioxides such as 6-methyl-3,4-dihydro-1,2,3-oxathiazin-4-one-2,2-dioxide, 6-ethyl-3,4-dihydro-1,2,3-oxathiazin-4-one-2,2-dioxide, 6-n-propyl-3,4-dihydro-1,2,3-oxathiazin-4-one-2,2-dioxide, and 6-i-propyl-3,4-dihydro-1,2,3-oxathiazin-4-one-2,2-dioxide; 6-aryl-3,4-dihydro-1,2,3-oxathiazin-4-one-2,2-dioxides such as 6-phenyl-3,4-dihydro-1,2,3,-oxathiazin-4-one-2,2-dioxide; 5,6-di$C_{1-4}$ alkyl-3,4-dihydro-1,2,3-oxathiazin-4-one-2,2-dioxides such as 5-methyl-6-methyl-3,4-dihydro-1,2,3,-oxathiazin-4-one-2,2-dioxide, and 5-methyl-6-ethyl-3,4-dihydro-1,2,3-oxathiazin-4-one-2,2-dioxide; 5-aryl-6-$C_{1-4}$ alkyl-3,4-dihydro-1,2,3-oxathiazin-4-one-2,2-dioxides such as 5-phenyl-6-methyl-3,4-dihydro-1,2,3-oxathiazin-4-one-2,2-dioxide; 5-$C_{1-4}$ alkyl-6-aryl-3,4-dihydro-1,2,3-oxathiazin-4-one-2,2-dioxides such as 3-methyl-6-phenyl-3,4-dihydro-1,2,3-oxathiazin-4-one-2,2-dioxide; 6-$C_{3-8}$ cycloalkyl-3,4-dihydro-1,2,3-oxathiazin-4-one-2,2-dioxides such as 6-cyclopentyl-3,4-dihydro-1,2,3-oxathiazin-4-one-2,2-dioxide, and 6-cyclohexyl-3,4-dihydro-1,2,3-oxathiazin-4-one-2,2-dioxid; 5-$C_{3-8}$ cycloalkyl-6-$C_{1-4}$ alkyl-3,4-dihydro-1,2,3-oxathiazin-4-one-2,2-dioxides such as 5-cyclopentyl-6-methyl-3,4-dihydro-1,2,3-oxathiazin-4-one-2,2-dioxide, and 5-cyclohexyl-6-methyl-3,4-dihydro-1,2,3-oxathiazin-4-one-2,2-dioxide; 5-$C_{1-4}$ alkyl-6-$C_{3-8}$ cycloalkyl-3,4-dihydro-1,2,3-oxathiazin-4-one-2,2-dioxides such as 5-methyl-6-cyclopentyl-3,4-dihydro-1,2,3-oxathiazin-4-one-2,2-dioxide and 5-methyl-6-cyclohexyl-3,4-dihydro-1,2,3-oxathiazin-4-one-2,2-dioxide; 6-$C_{2-4}$ alkenyl-3,4-dihydro-1,2,3-oxathiazin-4-one-2,2-dioxides such as 6-vinyl-3,4-dihydro-1,2,3-oxathiazin-4-one-2,2-dioxide; 6-$C_{2-6}$ acyl-3,4-dihydro-1,2,3-oxathiazin-4-one-2,2-dioxides such as 6-acetyl-3,4-dihydro-1,2,3-oxathiazin-4-one-2,2-dioxide; and salts of these compounds.

Specifically, 3,4-dihydro-1,2,3-oxathiazin-4-one-2,2-dioxide compounds in Formula (2) wherein $R^1$ is methyl group (for example, 6-methyl-3,4-dihydro-1,2,3-oxathiazin-4-one-2,2-dioxide) are preferred, because a part of physiologically acceptable salts thereof (for example, salts with Na, K, and Ca) are used as sweeteners in the food industry. Among them, the salt with potassium is specifically useful as Acesulfame (Acesulfame K).

EXAMPLES

Hereinafter, the present invention will be described in further detail with reference to examples, which are not intended to limit the scope of the invention.

Example 1

A reaction was carried out using, as a reactor, a stainless steel tube with an inner diameter of 4 mm and an effective length of 2 m and equipped with a Kenics static mixer as a mixer for raw materials (premixer). The Kenics static mixer had an inner diameter of 3.4 mm and a length of 10 cm and contained 17 elements. In 1,885 g of dichloromethane, 0.47 mol of triethylammonium acetoacetamide-N-sulfonate was dissolved and the whole was cooled to −10° C. Separately, 2.70 mmol of sulfuric anhydride was dissolved in 1,784 g of dichloromethane and similarly the whole was cooled to −10° C. Into the reactor immersed in a refrigerant at −30° C., the solution of triethylammonium acetoacetamide-N-sulfonate and the solution of sulfuric anhydride were continuously fed for 10 minutes at speeds of 201 g/min and 200 g/min, respectively. The residence time was 5.1 seconds. The reaction mixture was continuously taken out from the reactor and fed into a 2 L separable flask while being stirred at 500 rpm, and, for hydrolysis, 40% by weight of an aqueous solution of sulfuric acid was fed into the flask at a speed of 37 g/min simultaneously with the reaction mixture. Hydrolysis was carried out at 15 to 25° C. and the reaction mixture was continuously taken out, leaved, and separated into a dichloromethane phase liquid and an aqueous phase liquid. The concentration of sulfuric acid in the aqueous phase liquid was 52% by weight. An absorptiometric analysis of the dichloromethane phase liquid showed that the absorbance was 0.531 at 344 nm. An HPLC determination of 6-methyl-3,4-dihydro-1,2,3-oxathiazin-4-one-2,2-dioxide contained in the dichloromethane phase liquid showed that the yield was 70% (on the basis of triethylammonium acetoacetamide-N-sulfonate).

Example 2

A reaction was carried out using, as a reactor, a stainless steel tube with an inner diameter of 4 mm and an effective length of 2 m and equipped with a Kenics static mixer as a mixer for raw materials (premixer). The Kenics static mixer had an inner diameter of 3.4 mm and a length of 10 cm and contained 17 elements. In 1,885 g of dichloromethane, 0.47 mol of triethylammonium acetoacetamide-N-sulfonate was dissolved and the whole was cooled to −10° C. Separately, 2.70 mmol of sulfuric anhydride was dissolved in 1,784 g of dichloromethane and similarly the whole was cooled to −10° C. Into the reactor immersed in a refrigerant at −30° C., the solution of triethylammonium acetoacetamide-N-sulfonate and the solution of sulfuric anhydride were continuously fed for 10 minutes at speeds of 201 g/min and 200 g/min, respectively. The residence time was 5.1 seconds. The reaction mixture was continuously taken out from the reactor and fed into a 2 L separable flask while being stirred at 500 rpm. For hydrolysis, 40% by weight of an aqueous solution of sulfuric acid was fed into the flask at a speed of 37 g/min simultaneously with the reaction mixture. Hydrolysis was carried out at 15 to 25° C. and the reaction mixture was continuously taken out, leaved, and separated into a dichloromethane phase liquid and an aqueous phase liquid. The concentration of sulfuric acid in the aqueous phase liquid was 52% by weight. To the taken dichloromethane phase liquid, 75% by weight of an aqueous solution of sulfuric acid was added with 0.05 part by weight per one part by weight of the dichloromethane phase liquid, and the whole was stirred sufficiently. After stirring, the reaction mixture was leaved and subjected to liquid-liquid separation. An absorptiometric analysis of the obtained organic phase liquid (dichloromethane phase liquid) showed that the absorbance was 0.261 at 344 nm. An HPLC determination of 6-methyl-3,4-dihydro-1,2,3-oxathiazin-4-one-2,2-dioxide contained in the organic phase liquid (dichloromethane phase liquid) showed that the yield was 65% (on the basis of triethylammonium acetoacetamide-N-sulfonate). The yield was 5% lower in the washing process, however the washing solution after the washing (aqueous sulfuric acid phase liquid) may be used as a part of the aqueous solution of sulfuric acid for the hydrolysis in the hydrolysis process. Thus, the whole amount of 6-methyl-3,4-dihydro-1,2,3-oxathiazin-4-one-2,2-dioxide contained in the washing solution can be recovered.

Comparative Example 1

A reaction was carried out using, as a reactor, a stainless steel tube with an inner diameter of 4 mm and an effective length of 2 m and equipped with a Kenics static mixer as a mixer for raw materials (premixer). The Kenics static mixer had an inner diameter of 3.4 mm and a length of 10 cm and contained 17 elements. In 3,390 g of dichloromethane, 0.82 mol of triethylammonium acetoacetamide-N-sulfonate was dissolved and the whole was cooled to −10° C. Separately, 4.90 mmol of sulfuric anhydride was dissolved in 3,241 g of dichloromethane and similarly the whole was cooled to −10° C. Into the reactor immersed in a refrigerant at −30° C., the solution of triethylammonium acetoacetamide-N-sulfonate and the solution of sulfuric anhydride were continuously fed for 10 minutes at speeds of 362 g/min and 363 g/min, respectively. The residence time was 2.8 seconds. The reaction mixture was continuously taken out from the reactor and fed into a 2 L separable flask while being stirred at 500 rpm, and water for hydrolysis was fed into the flask at a speed of 100 g/min simultaneously with the reaction mixture. Hydrolysis was carried out at 15 to 25° C. and the reaction mixture was continuously taken out, leaved, and separated into a dichloromethane phase liquid and an aqueous phase liquid. The concentration of sulfuric acid in the aqueous phase liquid was 26% by weight. An absorptiometric analysis of the dichloromethane phase liquid showed that the absorbance was 0.845 at 344 nm. An HPLC determiation of 6-methyl-3 4-dihydro-1,2,3-oxathiazin-4-one-2,2-dioxide contained in the dichloromethane showed that the yield was 70% (on the basis of triethylammonium acetoacetamide-N-sulfonate).

INDUSTRIAL APPLICABILITY

A method for producing 3,4-dihydro-1,2,3-oxathiazin-4-one-2,2-dioxide compounds or salts thereof which are useful as sweeteners or raw materials therefor in food industry or intermediate materials for fine chemicals or the like, with significant reduction of purification loads may be provided.

What is claimed is:

1. A method for producing a 3,4-dihydro-1,2,3-oxathiazin-4-one-2,2-dioxide compound represented by the following formula (2)

[Formula 2]

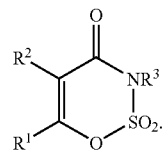

(2)

(wherein $R^1$ and $R^2$ are the same as or different from each other and are each hydrogen atom or an organic group inert to a reaction, $R^3$ is hydrogen atom or an organic group inert to the reaction)

or a salt thereof, by mixing a first solution of β-ketoamide-N-sulfonic acid represented by the following formula (1)

[Formula 1]

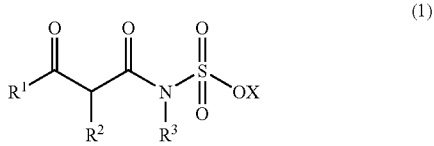

(1)

(wherein $R^1$, $R^2$ and $R^3$ are as defined above, and X is hydrogen atom)

or a salt thereof dissolved or dispersed in an inert solvent and a second solution of acid anhydride dissolved or dispersed in an inert solvent to be carried out cyclization, and subjecting the cyclized product to hydrolysis to obtain a mixed solution containing a liquid in organic phase and a liquid in aqueous phase, the method comprising at least one step selected from a group consisting of:

Step (A) of hydrolyzing the cyclized product by mixing with an aqueous solution of sulfuric acid so that a concentration of the sulfuric acid in the liquid in aqueous phase after the hydrolysis would become 30% by weight or more, and separating the mixed solution to the liquid in organic phase and the liquid in aqueous phase; and Step (B) of washing the liquid in organic phase after the hydrolysis with an aqueous solution of sulfuric acid with a concentration of 30% by weight or more.

2. The method for producing the 3,4-dihydro-1,2,3-oxathiazin-4-one-2,2-dioxide compound or the salt thereof of claim 1, wherein a concentration of the aqueous solution of sulfuric acid used in Step (A) is 15 to 50% by weight.

3. The method for producing the 3,4-dihydro-1,2,3-oxathiazin-4-one-2,2-dioxide compound or the salt thereof of claim 1, wherein a concentration of the aqueous solution of sulfuric acid used in Step (B) is 45 to 80% by weight.

4. The method for producing the 3,4-dihydro-1,2,3-oxathiazin-4-one-2,2-dioxide compound or the salt thereof of claim 1 or 3, wherein the aqueous solution of sulfuric acid used in Step (A) is a solution obtained in Step (B) after washing.

* * * * *